United States Patent
Li et al.

(10) Patent No.: US 10,900,028 B2
(45) Date of Patent: Jan. 26, 2021

(54) **HEPARINASE-PRODUCING *PSEUDOMONAS STUTZERI* STRAIN AND HEPARINASE DERIVED THEREFROM**

(71) Applicant: Shenzhen Hepalink Pharmaceutical Group Co., Ltd., Guangdong (CN)

(72) Inventors: Li Li, Shenzhen (CN); Jiake Bai, Shenzhen (CN); Jinliang Gao, Shenzhen (CN); Xiaolai Ma, Shenzhen (CN)

(73) Assignee: Shenzhen Hepalink Pharmaceutical Group Co., Ltd., Shenzhen (CN)

( * ) Notice: Subject to any disclaimer, the term of this patent is extended or adjusted under 35 U.S.C. 154(b) by 0 days.

(21) Appl. No.: 16/472,771

(22) PCT Filed: Dec. 22, 2017

(86) PCT No.: PCT/CN2017/117986
§ 371 (c)(1),
(2) Date: Jun. 21, 2019

(87) PCT Pub. No.: WO2018/113775
PCT Pub. Date: Jun. 28, 2018

(65) Prior Publication Data
US 2020/0123524 A1    Apr. 23, 2020

(30) Foreign Application Priority Data

Dec. 22, 2016  (CN) .......................... 2016 1 1195653

(51) Int. Cl.
*C12N 9/88* (2006.01)
*C07K 14/21* (2006.01)
*C12R 1/38* (2006.01)

(52) U.S. Cl.
CPC .................. *C12N 9/88* (2013.01); *C12R 1/38* (2013.01); *C12Y 402/02007* (2013.01)

(58) Field of Classification Search
CPC .................................. C12N 9/88; C07K 14/21
See application file for complete search history.

(56) References Cited

U.S. PATENT DOCUMENTS

| | | | |
|---|---|---|---|
| 4,341,869 A | 7/1982 | Langer, Jr. et al. | |
| 5,145,778 A | 9/1992 | Bellamy et al. | |
| 6,217,863 B1 | 4/2001 | Godavarti et al. | |
| 2018/0051270 A1 | 2/2018 | Bai | |

FOREIGN PATENT DOCUMENTS

| | | |
|---|---|---|
| CN | 1429913 | 7/2003 |
| CN | 1699424 | 11/2005 |
| CN | 101608178 | 12/2009 |
| CN | 102533628 | 7/2012 |
| CN | 104630197 | 5/2015 |
| CN | 106497897 | 3/2017 |
| CN | 104593347 | 8/2018 |
| EP | 0058686 | 2/1986 |
| EP | 3266868 | 1/2018 |
| WO | WO-89/12692 | 12/1989 |
| WO | 9534635 | * 12/1995 |

OTHER PUBLICATIONS

Wu et al., "Controllable production of low molecular weight heparins by combinations of heparinase I/II/III," Carbohydrate Polymers, 2013; 101: pp. 484-492.
Supplementary European Search Report issued in related European Application No. 17884747, dated Jul. 14, 2020.
Sasisekharan et al., "Heparinase I from *Flavobacterium heparinum*: The Role of the Cysteine Residue in Catalysis as Probed by Chemical Modification and Site-Directed Mutagenesis," Biochemistry, 1995; 34(44): pp. 14441-14448.
Linhardt et al., "An Immobilized Microbial Heparinase for Blood Deheparinization," Applied Biochemistry and Biotechnology, 1984; 9(1): pp. 41-55.
Abirami et al., "Isolation and characterization of 37 kDa heparinase from the purple fluid of *Dolabella auricularia*," Indian Journal of Geo-Marine Sciences, 2011; 40(1): pp. 112-116.
Gao et al., "Strain Screening and Fermentation Conditions of a Novel Heparinase-Producing Strain," Acta Microbiologica Sinica, 1999: pp. 64-67. (English abstract attached).
Gao et al., "Production of a Novel Heparinase From *Sphingobacterium* sp.," Acta Microbiologica Sinica, 2003; 43(6): pp. 813-816. (English abstract attached).
"GenBank WP_013632863.1," GenBank, 2013.
International Search Report issued in PCT/CN2017/117986, dated Feb. 28, 2018.

* cited by examiner

*Primary Examiner* — Karen Cochrane Carlson
(74) *Attorney, Agent, or Firm* — Arnall Golden Gregory LLP (57) ABSTRACT

The invention relates to the field of bioengineering. In particular, the invention relates to a heparinase-producing *Pseudomonas stutzeri* strain and a heparinase derived therefrom. Furthermore, the invention relates to the preparation and use of the heparinase.

18 Claims, 2 Drawing Sheets
Specification includes a Sequence Listing.

SEQUENCE LISTING

<160> NUMBER OF SEQ ID NOS: 3

<210> SEQ ID NO 1
<211> LENGTH: 1971
<212> TYPE: DNA
<213> ORGANISM: Artificial Sequence
<220> FEATURE:
<223> OTHER INFORMATION: Description of Artificial Sequence: Synthetic
      encoding sequence of heparinase PShepI

<400> SEQUENCE: 1

| | | | | | |
|---|---|---|---|---|---|
| atgaaattga | aatttctata | tctgtttatc | ctactttcc | cactgtccgt | tatcgggcaa | 60 |
| aagaaatcca | gtatttctaa | ggatgatttt | gccatcctta | atctggatca | cccgggatta | 120 |
| gaaaaagtta | aacaattggt | ttccaaacaa | aaataccaag | aagcttccaa | aacgctgttg | 180 |
| aattattata | aaaagcgtac | agacattaaa | catccagatt | acaatcttgc | ggataaaggt | 240 |
| cggttttgg | gcaagaaatt | atccaaagat | aatcaagaaa | aggccgacaa | agggctagat | 300 |
| catcactttt | atgttcataa | aggttatggt | tactttgact | atggaaaaga | catcaactgg | 360 |
| gaatactggc | ctgttaagga | caacgaagta | agatggcaac | ttcatcgtca | ttattggtgg | 420 |
| actccaatgg | gtttagctta | ttggtcaagt | ggagatgaaa | aatatgctaa | agaatgggtc | 480 |
| gcacaatatg | tggactgggt | gaagaaaaac | cctaaaggac | tctccaagaa | gaatgaccgg | 540 |
| tttgcttggc | gtccattaga | ggtatcacat | cgtattcaag | aacagacagg | cttatttaat | 600 |
| atgttcttga | cttcgcctca | tttcacgccc | gaatttctga | tggtgttttt | aaacaactat | 660 |
| aataagcatg | caaaccatat | attagaaaat | tactcggaaa | agggcaacca | tttacttttc | 720 |
| gaagcacaac | gtatgattta | tgcaggtgcg | tttttcccgg | aattaaaaaa | tgcacctact | 780 |
| tggcgtaaaa | gcggaatcga | aatcttaaat | acagagataa | aaaagcagat | ctatccagat | 840 |
| ggtatgcagt | ttgaattatc | tcccaactac | cacaccgctg | ccattaatat | ctttttgaaa | 900 |
| gcactacgaa | tggcacaatt | ggcgaatatt | gaccatgagt | ttccgccatc | ttataaagat | 960 |
| attatagaaa | aaatgatcat | ggcgcaggta | aactttctt | ttccagacta | ttcatttccg | 1020 |
| atgtttggag | acgcgtgggt | agccgacaag | aaggtctcta | ttagaaactt | tcaggattgg | 1080 |
| cagaaggtat | ttccagaaaa | caacacaata | acctattatg | ctacagacgg | taaaaaagga | 1140 |
| gaaacacttc | cctttctttc | tcacggggttg | aaagatggcg | gattttacac | ctttcgaaac | 1200 |
| agctggaaag | ataacgccac | ggctatggta | ctcaaagcaa | gcccaccggc | tttctggcat | 1260 |
| agtcaaccgg | ataacggaac | atttgagtta | tgggtgaagg | gtagaaactt | tatgcctgat | 1320 |
| gcgggcgtat | ttgtttatgg | tggcgacgaa | gaaatcctaa | agctacggaa | ttggtaccgt | 1380 |
| cagacaaaaa | tccataagac | gttgacttta | aataacgagg | acatagaaat | caacgatgcg | 1440 |
| cagcttatta | actggcatac | ttctgacaaa | ctggatgttc | tggtctataa | aaatccaagt | 1500 |
| tatgcaggat | tgaatcatat | ccggacagtc | ttatttattg | atcaacaata | ttttatcatc | 1560 |
| ttagataaag | ctgaaggaaa | agatgtcggt | aaggtcggta | ttcacttcca | attggttgag | 1620 |
| aatagtaacc | cggtatacaa | taaccaacaa | aatagtgtta | ccacaaggtt | taaagatggt | 1680 |
| aataacctat | tcattcgcaa | ctttaatcaa | gaccaagcac | aattagcaga | agaagaagga | 1740 |

-continued

```
aaagtttctt acttctaccg gaccgaggta gaacgtcctg cttttgtatt tgaacaaaac    1800
aagacaaacg aaaatagtat aaattttgcc acagtgctct acccttatca aggagaacat    1860
gtaccaaata ttgtttttga agaagaaacg ggtaatgacc cagagagagg caatatccat    1920
ttctctattt ccgtagacgg aaaaaaacag acgattcagc atcgttttta a             1971
```

```
<210> SEQ ID NO 2
<211> LENGTH: 656
<212> TYPE: PRT
<213> ORGANISM: Artificial Sequence
<220> FEATURE:
<223> OTHER INFORMATION: Description of Artificial Sequence: Synthetic
      amino acid sequence of heparinase PShepI

<400> SEQUENCE: 2
```

Met Lys Leu Lys Phe Leu Tyr Leu Phe Ile Leu Leu Phe Pro Leu Ser
1               5                   10                  15

Val Ile Gly Gln Lys Lys Ser Ser Ile Ser Lys Asp Asp Phe Ala Ile
            20                  25                  30

Leu Asn Leu Asp His Pro Gly Leu Glu Lys Val Lys Gln Leu Val Ser
        35                  40                  45

Lys Gln Lys Tyr Gln Glu Ala Ser Lys Thr Leu Leu Asn Tyr Tyr Lys
    50                  55                  60

Lys Arg Thr Asp Ile Lys His Pro Asp Tyr Asn Leu Ala Asp Lys Gly
65                  70                  75                  80

Arg Phe Leu Gly Lys Lys Leu Ser Lys Asp Asn Gln Glu Lys Ala Asp
                85                  90                  95

Lys Gly Leu Asp His His Phe Tyr Val His Lys Gly Tyr Gly Tyr Phe
            100                 105                 110

Asp Tyr Gly Lys Asp Ile Asn Trp Glu Tyr Trp Pro Val Lys Asp Asn
        115                 120                 125

Glu Val Arg Trp Gln Leu His Arg His Tyr Trp Trp Thr Pro Met Gly
    130                 135                 140

Leu Ala Tyr Trp Ser Ser Gly Asp Glu Lys Tyr Ala Lys Glu Trp Val
145                 150                 155                 160

Ala Gln Tyr Val Asp Trp Val Lys Lys Asn Pro Lys Gly Leu Ser Lys
                165                 170                 175

Glu Asn Asp Arg Phe Ala Trp Arg Pro Leu Glu Val Ser His Arg Ile
            180                 185                 190

Gln Glu Gln Thr Gly Leu Phe Asn Met Phe Leu Thr Ser Pro His Phe
        195                 200                 205

Thr Pro Glu Phe Leu Met Val Phe Leu Asn Asn Tyr Asn Lys His Ala
    210                 215                 220

Asn His Ile Leu Glu Asn Tyr Ser Glu Lys Gly Asn His Leu Leu Phe
225                 230                 235                 240

Glu Ala Gln Arg Met Ile Tyr Ala Gly Ala Phe Phe Pro Glu Leu Lys
                245                 250                 255

Asn Ala Pro Thr Trp Arg Lys Ser Gly Ile Glu Ile Leu Asn Thr Glu
            260                 265                 270

Ile Lys Lys Gln Ile Tyr Pro Asp Gly Met Gln Phe Glu Leu Ser Pro
        275                 280                 285

Asn Tyr His Thr Ala Ala Ile Asn Ile Phe Leu Lys Ala Leu Arg Met
    290                 295                 300

Ala Gln Leu Ala Asn Ile Asp His Glu Phe Pro Pro Ser Tyr Lys Asp
305                 310                 315                 320

```
Ile Ile Glu Lys Met Ile Met Ala Gln Val Asn Phe Ser Phe Pro Asp
                325                 330                 335

Tyr Ser Phe Pro Met Phe Gly Asp Ala Trp Val Ala Asp Lys Lys Val
            340                 345                 350

Ser Ile Arg Asn Phe Gln Asp Trp Gln Lys Val Phe Pro Glu Asn Asn
        355                 360                 365

Thr Ile Thr Tyr Tyr Ala Thr Asp Gly Lys Lys Gly Glu Thr Leu Pro
    370                 375                 380

Phe Leu Ser His Gly Leu Lys Asp Gly Gly Phe Tyr Thr Phe Arg Asn
385                 390                 395                 400

Ser Trp Lys Asp Asn Ala Thr Ala Met Val Leu Lys Ala Ser Pro Pro
                405                 410                 415

Ala Phe Trp His Ser Gln Pro Asp Asn Gly Thr Phe Glu Leu Trp Val
            420                 425                 430

Lys Gly Arg Asn Phe Met Pro Asp Ala Gly Val Phe Val Tyr Gly Gly
        435                 440                 445

Asp Glu Glu Ile Leu Lys Leu Arg Asn Trp Tyr Arg Gln Thr Lys Ile
    450                 455                 460

His Lys Thr Leu Thr Leu Asn Asn Glu Asp Ile Glu Ile Asn Asp Ala
465                 470                 475                 480

Gln Leu Ile Asn Trp His Thr Ser Asp Lys Leu Asp Val Leu Val Tyr
                485                 490                 495

Lys Asn Pro Ser Tyr Ala Gly Leu Asn His Ile Arg Thr Val Leu Phe
            500                 505                 510

Ile Asp Gln Gln Tyr Phe Ile Ile Leu Asp Lys Ala Glu Gly Lys Asp
        515                 520                 525

Val Gly Lys Val Gly Ile His Phe Gln Leu Val Glu Asn Ser Asn Pro
    530                 535                 540

Val Tyr Asn Asn Gln Gln Asn Ser Val Thr Thr Arg Phe Lys Asp Gly
545                 550                 555                 560

Asn Asn Leu Phe Ile Arg Asn Phe Asn Gln Asp Gln Ala Gln Leu Ala
                565                 570                 575

Glu Glu Glu Gly Lys Val Ser Tyr Phe Tyr Arg Thr Glu Val Glu Arg
            580                 585                 590

Pro Ala Phe Val Phe Glu Gln Asn Lys Thr Asn Glu Asn Ser Ile Asn
        595                 600                 605

Phe Ala Thr Val Leu Tyr Pro Tyr Gln Gly Glu His Val Pro Asn Ile
    610                 615                 620

Val Phe Glu Glu Glu Thr Gly Asn Asp Pro Glu Arg Gly Asn Ile His
625                 630                 635                 640

Phe Ser Ile Ser Val Asp Gly Lys Lys Gln Thr Ile Gln His Arg Phe
                645                 650                 655

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis Tag

<400> SEQUENCE: 3

His His His His His His
1               5
```

HEPARINASE-PRODUCING *PSEUDOMONAS STUTZERI* STRAIN AND HEPARINASE DERIVED THEREFROM

SEQUENCE LISTING

The instant application contains a Sequence Listing which has been submitted in ASCII format via EFS-Web and is hereby incorporated by reference in its entirety. Said ASCII copy, created on Oct. 2, 2019, is named 022253_0101PTUS._SL.txt and is 9,123 bytes in size.

TECHNICAL FIELD

The invention relates to the field of bioengineering. In particular, the invention relates to a heparinase-producing *Pseudomonas stutzeri* strain and heparinase derived therefrom. Furthermore, the invention relates to the preparation and use of said heparinase.

BACKGROUND

Heparinase refers to an enzyme that is able to specifically break the glucosidic bond on the backbone of heparin and heparinoid. It is widely used, for example, to remove the remaining heparin from the blood, to prepare low molecular weight heparin, to study the heparin structure, or to conduct quality testing of heparin and the like. Heparinase was originally discovered and isolated from *Flavobacterium heparinum*, and subsequently found in some microbial and animal tissues. There are more than 20 kinds of heparinases reported in literatures. For example, Yang V. C. found heparinase I, II, III from *Flavobacterium heparinum*; Robert W. Bellamy et al. found from *Bacillus* BH100 (FERM BP-2613) a heparinase secreted to the extracellular; and Wan-Seok Kim et al. found a heparin lyase from *Bacteroides stercoris* HJ-15 (Carbohydrate Research, 2012, 359: 37-43). Chinese patent application 201410839278.8 disclosed novel heparinases SDhepI and SDhepII obtained from the bacteria of *Sphingobacterium daejeonense*. Chinese patent application 201510040524.8 disclosed a novel heparinase CMHEPI obtained from the bacteria of *Chryseobacterium meningosepticum*. All the above heparinases are different to each other.

The most widely studied and widely used heparinases are heparinase I, heparinase II and heparinase III from *Flavobacterium heparinum*, which are monomeric proteins with molecular weights of approximately 43, 78, 66 kDa, respectively, and isoelectric points of around 9.0. The discovery of heparinase has played an important role in promoting structure research and quality testing of heparin. Heparinases I, II and III produced from *Flavobacterium heparinum* have been used for quality testing of heparin and production of low molecular weight heparin.

There are various heparinases produced by various heparinase-producing microorganisms obtained from nature, with which various products can be obtained by enzymolysis of heparin. In order to fulfill various needs in research and industry, new heparinases are still needed in the art.

DESCRIPTION OF THE INVENTION

In a first aspect, the present invention provides a *Pseudomonas stutzeri* strain deposited at the China Center for Type Culture Collection under the Accession Number CCTCC M 2017174.

This strain is a *Pseudomonas stutzeri* strain which was isolated in the field by the present inventors and has the activity of lysing heparin or a derivative thereof, and is named as Z7. The present inventors further isolated and purified two novel intracellular heparinases PShepI and PShepII from the strain. These two novel heparinases have physicochemical properties different from those of the currently known heparinases, and have high selectivity for the lysing site during the enzymolysis of heparin, which can be used for quality testing of the heparin products or for the preparation of low molecular or ultra-low molecular weight heparin.

Thus, in another aspect, the invention also encompasses the application and method for producing a heparinase with the Z7 *Pseudomonas stutzeri* strain. For example, the method for producing heparinase from the Z7 strain may include culturing the Z7 *Pseudomonas stutzeri* strain, lysing the cultured cells of the *Pseudomonas stutzeri* strain, and isolating and/or purifying the heparinase from the lysate. Preferably, the culture is carried out under a suitable condition. For example, the Z7 *Pseudomonas stutzeri* strain may be cultured at a temperature of about 30° C. In some embodiments, the culture is fermentation. Suitable culture/fermentation conditions for *Pseudomonas stutzeri* strain can be readily determined by those skilled in the art. The lysis can be carried out by a variety of methods known in the art for disrupting cells, such as freeze-thaw lysis, sonication, high pressure treatment, and the like. In addition, one skilled in the art can select a suitable method for isolating and/or purifying heparinase from cell lysates according to specific properties of the heparinase, such as the molecular weight, isoelectric point, etc. For example, a specific heparinase can be isolated and/or purified by a molecular sieve, anion exchange chromatography, cation exchange chromatography, heparinase affinity chromatography, and the like.

In another aspect, the invention provides a heparinase derived from a *Pseudomonas stutzeri* strain, preferably from the Z7 *Pseudomonas stutzeri* strain of the invention. The heparinase is, for example, PShepI or PShepII.

In some embodiments, the heparinase (such as PShepI) has one or more characteristics selected from the group consisting of:

i) a molecular weight of 74791 Da;
ii) an isoelectric point of about 7.77;
iii) a HEP/HS enzyme activity ratio of about 0.87:1 with heparin (HEP) and HS (heparan sulfate) as the substrates respectively;
iv) a Michaelis constant of about 4.20 with HEP as the substrate;
v) a Michaelis constant of about 0.28 with HS as the substrate; and
vi) when HEP is used as the substrate, the major heparin disaccharide products are IIS and IS.

In some embodiments, the heparinase (such as PShepI) can be obtained, for example, by a method comprising the following steps:

a) culturing the Z7 *Pseudomonas stutzeri* strain of the present invention and collecting the cultured bacterial cells;
b) resuspending and lysing the cells obtained in step a) in a buffer and collecting the supernatant after centrifugation;
c) precipitating the supernatant obtained in step b) with ammonium sulfate of 20% to 100% saturation, and dissolving the resulting precipitate in a buffer and dialyzing against the buffer;
d) loading the product of step c) onto an anion exchange column, including but not limited to Q-Sepharose Fast Flow, Q-Sepharose Big Beads, Q-Sepharose XL or Q-Sepharose High Performance columns, equilibrating with a buffer, and collecting the loading flow-through and the equilibrating flow-through, and dialyzing the collected loading flow-through and equilibrating flow-through against the buffer; and e) loading the product of step d) onto a cation exchange column such as a SP-Sepharose Fast Flow column, and equilibrating the column with a buffer, performing linear gradient elution with a sodium chloride solution (e.g. a 0-0.5M sodium chloride solution) based on the same buffer, collecting fractions of the eluate with heparinase activity, and optionally dialyzing the collected eluate against the buffer.

Various methods are known in the art for measuring the activity of the heparinase, such as the method described in Chinese Patent Application No. 201110241260.4. Thus, in the method of the present invention, the heparinase activity of every fraction in the chromatography steps can be monitored during preparation of the heparinase to collect the desired fractions.

PShepI is separated from PShepII after the crude separation with anion exchange column in the above step d), and as in step e), a large amount of undesired proteins are removed by the cation exchange column, the obtained PShepI is thus purified. However, it may further comprise one or more affinity chromatography steps to further purify the PShepI heparinase. The one or more affinity chromatography steps are performed using a heparinase affinity column such as a Cellufine Sulfate column or a heparin-conjugated CNBr-activated Sepharose CL-4B heparinase affinity column.

For example, in some preferred embodiments, the method further includes the steps of:

f) loading the product of step e) onto a heparinase affinity column such as a Cellufine Sulfate column or a heparin-conjugated CNBr-activated Sepharose CL-4B heparinase affinity column, and equilibrating the column with a buffer, performing linear gradient elution with a sodium chloride solution (e.g. a 0.15-0.6 M sodium chloride solution) based on the same buffer, collecting fractions of the eluate with heparinase activity, and optionally dialyzing the collected eluate against the buffer.

In some embodiments, the method further comprises the step of concentrating the product.

In some embodiments, the buffer is a Tris-HCl buffer. In some embodiments, the buffer is a $CaCl_2$-containing Tris-HCl buffer. In some embodiments, the concentration of Tris-HCl is from about 10 mM to about 50 mM, preferably about 25 mM. In some embodiments, the concentration of $CaCl_2$ in the buffer is from about 1 mM to about 50 mM, preferably about 10 mM. In some embodiments, the pH of the buffer ranges from about 7.0 to about 7.5, preferably about 7.0. In some embodiments, a same buffer is used in all steps.

In other embodiments, the heparinase (such as PShepII) has one or more characteristics selected from the group consisting of:

i) a molecular weight of 94716 Da;
ii) an isoelectric point of about 5.76;
iii) a HEP/HS enzyme activity ratio of about 1:4.3 with heparin (HEP) and HS (heparan sulfate) as the substrates respectively;
iv) a Michaelis constant of about 0.09 with HEP as the substrate;
v) a Michaelis constant of about 0.25 with HS as the substrate.

In some embodiments, the heparinase (such as PShepII) can be obtained, for example, by a method comprising the following steps:

a) culturing the Z7 *Pseudomonas stutzeri* strain of the present invention and collecting the cultured bacterial cells;

b) resuspending and lysing the cells obtained in step a) in a buffer and collecting the supernatant after centrifugation;

c) precipitating the supernatant obtained in step b) with ammonium sulfate of 20% to 100% saturation, and dissolving the resulting precipitate in a buffer and dialyzing against the buffer;

d) loading the product of step c) onto an anion exchange column, including but not limited to Q-Sepharose Fast Flow, Q-Sepharose Big Beads, Q-Sepharose XL or Q-Sepharose High Performance columns, and equilibrating the column with a buffer, performing linear gradient elution with a sodium chloride solution (e.g. a 0-0.5M sodium chloride solution) based on the same buffer, collecting fractions of the eluate with heparinase activity, and optionally dialyzing the collected eluate against the buffer.

Various methods are known in the art for measuring the activity of the heparinase, such as the method described in Chinese Patent Application No. 201110241260.4. Thus, in the method of the present invention, the heparinase activity of every fraction in the chromatography steps can be monitored during preparation of the heparinase to collect the desired fractions.

After the crude separation on the anion exchange column in the above step d), PShepI and PShepII are separated, and the PShepII so obtained is already purified. However, it may further comprise one or more affinity chromatography steps to further purify the PShepII heparinase. The one or more affinity chromatography steps are performed using a heparinase affinity column such as a Cellufine Sulfate column or a heparin-conjugated CNBr-activated Sepharose CL-4B heparinase affinity column.

For example, in some preferred embodiments, the method further includes the steps of:

e) loading the product of step d) onto a heparinase affinity column (such as a Cellufine Sulfate column), and equilibrating the column with a buffer, performing linear gradient elution with a sodium chloride solution (e.g. a 0.05-0.5M sodium chloride solution) based on the same buffer, collecting fractions of the eluate with heparinase activity, and dialyzing the collected eluate against the buffer;

f) loading the product of step e) onto a heparinase affinity column (e.g., a Cellufine Sulfate column), and equilibrating the column with a buffer, performing isocratic elution with a sodium chloride solution (e.g. a 2.5M sodium chloride solution) based on the same buffer, and collecting fractions of the eluate with heparinase activity;

g) loading the product of step f) onto a heparinase affinity column (such as a Cellufine Sulfate column), and equilibrating the column with a buffer, performing linear gradient elution with a sodium chloride solution (e.g. a 0-0.5M sodium chloride solution) based on the same buffer, collecting fractions of the eluate with heparinase activity, and optionally dialyzing the collected eluate against the buffer.

In some embodiments, the method further comprises the step of concentrating the product.

In some embodiments, the buffer is a Tris-HCl buffer. In some embodiments, the buffer is a $CaCl_2$-containing Tris-HCl buffer. In some embodiments, the concentration of Tris-HCl is from about 10 mM to about 50 mM, preferably about 25 mM. In some embodiments, the concentration of $CaCl_2$ in the buffer is from about 1 mM to about 50 mM, preferably about 10 mM. In some embodiments, the pH of the buffer ranges from about 7.0 to about 7.5, preferably about 7.0. In some embodiments, a same buffer is used in all steps.

In another aspect, the invention provides a method for producing a heparinase (such as PShepI), the method comprising the steps of:

a) culturing the *Pseudomonas stutzeri* strain of the present invention and collecting the cultured bacterial cells;

b) resuspending and lysing the cells obtained in step a) in a buffer and collecting the supernatant after centrifugation;

c) precipitating the supernatant obtained in step b) with ammonium sulfate of 20% to 100% saturation, and dissolving the resulting precipitate in a buffer and dialyzing against the buffer;

d) loading the product of step c) onto an anion exchange column, such as Q-Sepharose Fast Flow, Q-Sepharose Big Beads, Q-Sepharose XL or Q-Sepharose High Performance columns, equilibrating the column with a buffer, and collecting the loading flow-through and the equilibrating flow-through, and dialyzing the collected loading flow-through and equilibrating flow-through against the buffer;

e) loading the product of step d) onto a cation exchange column such as a SP-Sepharose Fast Flow column, and equilibrating the column with a buffer, performing linear gradient elution with a sodium chloride solution (e.g. a 0-0.5M sodium chloride solution) based on the same buffer, collecting fractions of the eluate with heparinase activity, and optionally dialyzing the collected eluate against the buffer.

In some embodiments, the method further comprises one or more affinity chromatography steps to further purify the heparinase, the one or more affinity chromatography steps using a heparinase affinity column such as a Cellufine Sulfate column or a heparin-conjugated CNBr-activated Sepharose CL-4B heparinase affinity column.

In some embodiments, the method further includes the steps of:

f) loading the product of step e) onto a heparinase affinity column such as a Cellufine Sulfate column or a heparin-conjugated CNBr-activated Sepharose CL-4B heparinase affinity column, and equilibrating the column with a buffer, performing linear gradient elution with a sodium chloride solution (e.g. a 0.15-0.6M sodium chloride solution) based on the same buffer, collecting fractions of the eluate with heparinase activity, and optionally dialyzing the collected eluate against the buffer.

In some embodiments, the method further comprises the step of concentrating the product.

In yet another aspect, the invention provides a method for producing a heparinase (such as PShepII), the method comprising the steps of:

a) culturing the *Pseudomonas stutzeri* strain of the present invention and collecting the cultured bacterial cells;

b) resuspending and lysing the cells obtained in step a) in a buffer and collecting the supernatant after centrifugation;

c) precipitating the supernatant obtained in step b) with ammonium sulfate of 20% to 100% saturation, and dissolving the resulting precipitate in a buffer and dialyzing against the buffer;

d) loading the product of step c) onto an anion exchange column, such as Q-Sepharose Fast Flow, Q-Sepharose Big Beads, Q-Sepharose XL or Q-Sepharose High Performance columns, and equilibrating the column with a buffer, performing linear gradient elution with a sodium chloride solution (e.g. a 0-0.5M sodium chloride solution) based on the same buffer, collecting fractions of the eluate with heparinase activity, and optionally dialyzing the collected eluate against the buffer.

In some embodiments, the method further comprises one or more affinity chromatography steps to further purify the heparinase, the one or more affinity chromatography steps using a heparinase affinity column such as a Cellufine Sulfate column or a heparin-conjugated CNBr-activated Sepharose CL-4B heparinase affinity column.

In some embodiments, the method further includes the steps of:

e) loading the product of step d) onto a heparinase affinity column (such as a Cellufine Sulfate column), and equilibrating the column with a buffer, performing linear gradient elution with a sodium chloride solution (e.g. a 0.05-0.5M sodium chloride solution) based on the same buffer, collecting fractions of the eluate with heparinase activity, and dialyzing the collected eluate against the buffer;

f) loading the product of step e) onto a heparinase affinity column (e.g., a Cellufine Sulfate column), and equilibrating the column with a buffer, performing isocratic elution with a sodium chloride solution (e.g. a 2.5M sodium chloride solution) based on the same buffer, and collecting fractions of the eluate with heparinase activity; and g) loading the product of step f) onto a heparinase affinity column (such as a Cellufine Sulfate column), and equilibrating the column with a buffer, performing linear gradient elution with a sodium chloride solution (e.g. a 0-0.5M sodium chloride solution) based on the same buffer, collecting fractions of the eluate with heparinase activity, and optionally dialyzing the collected eluate against the buffer.

In some embodiments, the method further comprises the step of concentrating the product.

In some embodiments of the above methods for producing the heparinase of the invention, the buffer is a Tris-HCl buffer. In some embodiments, the buffer is a CaCl$_2$)-containing Tris-HCl buffer. In some embodiments, the concentration of Tris-HCl is from about 10 mM to about 50 mM, preferably about 25 mM. In some embodiments, the concentration of CaCl$_2$) in the buffer is from about 1 mM to about 50 mM, preferably about 10 mM. In some embodiments, the pH of the buffer ranges from about 7.0 to about 7.5, preferably about 7.0. In some embodiments, a same buffer is used in all steps.

The inventors further identified the sequence of PShepI, the amino acid sequence of which is shown in SEQ ID NO: 2, and the coding nucleotide sequence thereof is shown in SEQ ID NO: 1.

Accordingly, in another aspect, the invention further provides a heparinase comprising an amino acid sequence having at least 75%, at least 80%, at least 85%, at least 90%, at least 91%, at least 92%, at least 93%, at least 94%, at least 95%, at least 96%, at least 97%, at least 99% sequence identity to the amino acid sequence shown in the SEQ ID NO:2, or comprising an amino acid sequence with 1, 2, 3, 4, 5, 6, 7, 8, 9 or 10 amino acid substitutions, deletions or additions compared with the amino acid sequence shown in the SEQ ID NO:2. Preferably, the heparinase retains or substantially retains the activity of the PShepI. In some embodiments, the heparinase is derived or originated from or isolated from *Pseudomonas stutzeri*. In some embodiments, the heparinase is recombinantly produced, i.e., the heparinase is a recombinant heparinase. Methods for recombinant production of a heparinase are further described below.

When the term "comprising" is used herein to describe the sequence of a protein or nucleic acid, the protein or nucleic acid may consist of the sequence or may have additional amino acids or nucleotides at one or both ends of the protein or nucleic acid, but still have the activity described herein.

In some embodiments, the heparinase of the invention may comprise an additional linker or be fused to another tag protein. Such a linker and/or tag may facilitate the production of the heparinase of the present invention in a host cell of interest, increase the amount of expression or increase the soluble expression, facilitate the isolation and purification of the heparinase, but do not substantially affect the activity of the heparinase. Various such linkers and/or tags are known in the art. Suitable linkers and/or tags include, for example, 6×His (SEQ ID NO: 3), GST (glutathione transferase), MBP (maltose-binding protein), and the like. Suitable linkers and/or tags may generally be obtained by selecting a suitable commercial expression vector.

Suitable conservative amino acid substitutions in peptides or proteins are known to those skilled in the art and can generally be carried out without altering the biological activity of the resulting molecule. In general, one skilled in the art would recognize that a single amino acid substitution in a non-essential region of a polypeptide does not substantially alter the biological activity (see, for example, Watson et al., Molecular Biology of the Gene, 4th Edition, 1987, The Benjamin/Cummings Pub Co., p. 224).

The sequence "identity" has a well-known meaning in the art, and the percentage of sequence identity between two nucleic acid or polypeptide molecules or regions can be calculated using the disclosed techniques. The sequence identity can be measured along the entire length of a polynucleotide or polypeptide or along a region of the molecule. (See, for example: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G, Academic Press, 1987; and Sequence Analysis Primer, Gribskov, M. and Devereux, J., eds., M Stockton Press, New York, 1991). Although there are many methods for measuring the identity between two polynucleotides or polypeptides, the term "identity" is well known to the skilled person (Carrillo, H. & Lipman, D., SIAM J Applied Math 48:1073 (1988)).

In another aspect, the invention provides an isolated polynucleotide comprising a nucleotide sequence encoding the heparinase of the invention described above.

As used herein, "polynucleotide" refers to a macromolecule of a plurality of nucleotides joined by 3'-5'-phosphodiester bonds, wherein the nucleotide includes ribonucleotide and deoxyribotide. The sequence of the polynucleotide of the invention may be codon-optimized for different host cells, such as $E.$ $coli$, to improve the expression of the heparinase. Methods for performing the codon-optimization are known in the art.

In some specific embodiments of this aspect, the polynucleotide comprises the nucleotide sequence shown in the SEQ ID NO: 1.

In another aspect, the invention provides an expression construct comprising the polynucleotide of the invention operably linked to an expression control sequence.

In the expression construct of the invention, the sequence of the polynucleotide encoding the heparinase of the invention is operably linked to an expression control sequence so as to allow the desired transcription and production of the heparinase in the host cell. Suitable expression control sequences include, but are not limited to, a promoter, an enhancer, a ribosome action site such as a ribosome binding site, a polyadenylation site, a transcriptional splicing sequence, a transcriptional termination sequence and a sequence for stabilizing mRNA, and the like.

As used herein, the term "operably linked" refers to the attachment of a control sequence to a nucleotide sequence of interest such that transcription of the nucleotide sequence of interest is controlled and regulated by the transcriptional control sequence. Techniques for operably linking the expression control sequence to the nucleotide sequence of interest are known in the art.

The vectors for use in the expression construct of the invention include those which autonomously replicate in a host cell, such as a plasmid vector; and also the vectors that are capable of integrating into the DNA of the host cell and replicating with the DNA of the host cell. Many vectors suitable for the present invention are commercially available. In a specific embodiment, the expression construct of the invention is derived from the pET30a from Novagen Corporation. In a specific embodiment, the expression construct of the invention is derived from the pET28a from Novagen Corporation.

In another aspect, the invention provides a host cell comprising a polynucleotide comprising a nucleotide sequence encoding the heparinase of the invention or transformed with an expression construct comprising the polynucleotide, wherein the host cell is capable of expressing the heparinase of the invention. Preferably, the host cell is a recombinant host cell.

The host cell for expressing the heparinase of the invention includes a prokaryote, yeast, and higher eukaryote. An exemplary prokaryotic host includes bacteria of the genus *Escherichia, Bacillus, Salmonella*, and *Pseudomonas* and *Streptomyces*. In a preferred embodiment, the host cell is a cell of the genus *Escherichia*, preferably *E. coli*. In a specific embodiment of the invention, the host cell used is a cell of the *E. coli* BL21 (DE3) strain.

The recombinant expression construct of the invention may be introduced into a host cell by one of the various well-known techniques, including but not limited to: heat shock transformation, electroporation, DEAE-dextran transfection, microinjection, lipid body-mediated transfection, calcium phosphate precipitation, protoplast fusion, microprojectile bombardment, viral transformation and the like.

In another aspect, the invention provides a method for recombinantly producing a heparinase, comprising:

a) culturing the host cell of the invention under a condition that allows the expression of the heparinase;

b) obtaining the heparinase expressed by the host cell from the culture resulting from step a); and c) optionally further purifying the heparinase obtained from step b).

In still another aspect, the present invention provides a use of the *Pseudomonas stutzeri* strain of the present invention, the heparinase of the present invention or the host cell of the present invention in producing a low molecular weight heparin or an ultra-low molecular weight heparin or in testing the quality of a heparin, low molecular heparin or an ultra-low molecular weight heparin.

In still another aspect, the invention provides a method for producing a low molecular weight heparin or an ultra-low molecular weight heparin, comprising the steps of contacting the heparin with the *Pseudomonas stutzeri* strain of the invention, the heparinase of the invention or the host cell of the invention.

EXAMPLES

The invention is further described below by examples, but is not intended to be limited to such examples.

In the examples of the present application, the enzyme activity for the heparin (HEP) and the heparin sulfate (HS) is determined by reference to Chinese Patent Application No. 201110241260.4. Methods for determining the protein content and the enzyme purity are described in Carbohydrate Research, 2012, 359: 37-43.

Method for detecting the desulfurase: 52 mIU heparinase was used to react with 10 μl of 1 mg/ml I-S, and 25 mM Tris-HCl (containing 10 mM $CaCl_2$, with pH of 7.0) buffer was added to bring the reaction system to 200 μl. The reaction was performed at room temperature for 24 hours, and heparinase was inactivated by boiling in a 100° C. water bath for 5 min, and loaded onto a HPLC-SAX column to determine the relative percentage of II-S and I-S.

Example 1: Isolation and Identification of a New *Pseudomonas stutzeri* Strain Screening of Heparinase-Producing Strains Soil samples were collected from the west of Chengguan Town, Yunmeng County, Hubei Province, China; heparin was dissolved in purified water (less than or equal to 8 g/L), poured into each soil sample to keep each soil sample moist. The samples were so treated once to twice a week (the frequency depending on the dryness of the soil sample), and cultured for 35-40 days. Two spoons of soil samples were taken with a weighing spoon and added to autoclaved purified water, and shook (150 rpm) for 2-3 hours in a shaker at 30° C. to allow the soil samples uniformly distributed in the purified water. 20 ml of the purified water with the dissolved soil sample was pipetted into 200 ml autoclaved seed culture medium, shook at 30° C. in a shaker for 16 hours (150 rpm), and then 2.5 ml bacteria liquid was pipetted into a 4 ml quartz cuvette to test its OD600 to determine the growth of the strain. If the OD600 of the strain in the previous step is greater than 2.4, then 20 ml bacteria liquid was pipetted into 200 ml of autoclaved fermentation medium, shook at 30° C. for 24 hours in a shaker (150 rpm), and then 3 ml of the bacteria liquid was pipetted as a sample.

2.5 ml bacteria liquid was pipetted from the 3 ml bacteria liquid sample and added to a 4 ml quartz cuvette to detect its OD600 to determine the growth of the strain. If the OD600 of the strain is greater than 2.0, it means the strain grows well in the fermentation medium. At the same time, the remaining 0.5 ml bacteria liquid was centrifuged (4° C., 5000 g, 5 min) to obtain a supernatant, and the supernatant was then diluted by 10 times with ultrapure water for use. Heparin was dissolved in ultrapure water and diluted to 0.1 mg/ml, 0.2 mg/ml, 0.3 mg/ml, 0.4 mg/ml, 0.5 mg/ml, 0.6 mg/ml, 0.7 mg/ml, 0.8 mg/ml. 2.5 ml of Azure A solution (20 mg/L) and 25 μl of the heparin aqueous solution were added into a cuvette and mixed to detect the absorption value at 620 nm, and then a standard curve was plotted. After that, the absorption value of the diluted strain supernatant at 620 nm was detected in the same manner, and the heparin concentration was calculated. If the heparin concentration is less than 5.5 g/L, it is considered that the bacteria liquid contains a strain capable of consuming heparin (heparinase-producing). The bacterial liquid resulting in a heparin concentration of less than 5.5 g/L was diluted and plated (10e-6, 10e-7, 10e-8, 10e-9), and after about 3-4 days, colonies or microbial population were observed on the surface of the solid medium. A plurality of colonies were picked up from the surface of the medium in the previous step to carry out plate streaking, and after 2-3 days of culture, relatively pure single colonies were selected.

The colonies obtained by plate streaking were scraped off and added to the seed medium and cultured for 16 hours, and then transferred to a fermentation medium (10% inoculum) for about 24 hours. A sample was taken from the fermentation medium, and its heparin consumption was detected by referring to the aforementioned steps. If the heparin consumption is still less than 5.5 g/L, then the steps of diluting and coating and plate streaking were repeated for further purifying the strain until a pure single colony is obtained. The re-screening can be carried out several times according to the purity of the colony. In this experiment, all the soil samples with desired activity were screened 3 times.

Single colonies were streaked on a slant medium and stored in a liquid medium. The streaked slant medium was stored in a cold storage, and the cultured bacteria liquid was stored in a 50% glycerin and stored in a refrigerator at −20° C.

Identification of Heparinase-Producing Strains

The heparinase-producing strain was purified to a pure single colony, and then sent to the Guangdong Provincial Microbial Analysis and Testing Center for identification.

Through bacterial microscopic observation, physical and chemical property analysis and 16S rDNA sequence alignment, it was confirmed that the present inventors screened out a *Pseudomonas stutzeri* strain capable of producing heparinase, which was named as Z7. The strain was deposited at the China Center for Type Culture Collection (Wuhan University, Wuhan, China, 430072) on Apr. 10, 2017 under the Budapest Treaty under the accession number: CCTCC M 2017174, and it is confirmed that: (a) during the pendency of this application, access to the deposited organism will be afforded to the Commissioner upon request; (b) all restrictions upon availability to the public of the deposited materials will be irrevocably removed upon granting of the patent, subject to 37 C.F.R., § 1.808(b); (c) the deposit will be maintained for a period of 30 years or 5 years after the last request or for the effective life of the patent, whichever is longer; and (d) the deposit will be replaced if it should ever become non-viable.

It is known that *Pseudomonas stutzerii* is basically non-pathogenic to human and can degrade carrageenan. It is a bacterium effective for sewage treatment and soil waste treatment, and is a denitrifying bacteria with the ability to corrode metals. However, there have been no reports on the ability of *Pseudomonas stutzeri* to produce heparinase.

Identification of Heparinase Activity of Z7 Strain

The identified Z7 strain with the desired enzyme activity was fermented, and the activity for HEP and HS was measured after cell disruption (1 L fermented cells). The results are shown in

TABLE 1

| HEP and HS activity measured after fermentation and cell disruption of Z7 strain | |
|---|---|
| HEP enzyme activity (IU/L) | HS enzyme activity (IU/L) |
| 592.2 | 602.1 |

Example 2: Preparation of Heparinase from Z7 Strain and Activity Determination

Preparation of the Medium:

The formula of the seed medium: beef extract 5 g/L, peptone 10 g/L, yeast powder 5 g/L, sodium chloride 5 g/L, pH7.0; the formula of the fermentation medium: heparin 8 g/L, peptone 2 g/L, potassium dihydrogen phosphate 2.5 g/L, ammonium sulfate 1 g/L, magnesium sulfate 0.5 g/L, sodium chloride 5 g/L, pH 7.0; the solid medium is prepared by adding 20 g/L agar powder to the fermentation medium.
Fermentation of Strains and Preparation of Crude Enzyme Solution:

The Z7 Pseudomonas stutzeri strain was inoculated into the seed culture medium by scraping two rings of bacteria from the plate or the slant. After 16 hours of culture, the seed was added to a secondary liquid seed culture medium with a 15% inoculation amount, cultured for 1 day, and then inoculated into a 2 L fermentation medium with a 20% inoculation amount, cultured for 1 day. The bacteria cells were collected by centrifuging at 3800 rpm, 4° C. for 45 minutes, and then the precipitate was suspended in a 25 mM Tris-HCl buffer (containing 10 mM $CaCl_2$, pH 7.0), lysed by a high pressure homogenizer at 4° C., 800 bar for 3-4 cycles, and centrifuged for 30 minutes (12000 rpm, 4° C.). The supernatant was precipitated with ammonium sulfate in an ice bath, and precipitate at 20%-100% ammonium sulfate saturation was collected and dissolved in 100 ml Tris-HCl buffer, and dialyzed overnight against the same buffer.
Preparation Method I Q-Sepharose Fast Flow column separation: The dialyzed crude enzyme solution after the previous step was loaded onto a 2.5×30 cm Q column equilibrated with a 25 mM Tris-HCl (containing 10 mM $CaCl_2$, pH 7.0) buffer. The column was equilibrated with 3 column volumes of the same buffer and eluted with a linear gradient of a buffer containing 0-0.5 M sodium chloride. One peak with desired activity was obtained, designated as PShepII. The loading flow-through and the equilibrating flow-through were detected and found to have heparinase activity, and the enzyme solution of this part was named as PShepI. The PShepI and PShepII fractions were collected and dialyzed against 2 L 25 mM Tris-HCl (containing 10 mM $CaCl_2$, pH 7.0) buffer overnight.

Purification of PShepI by Cellufine Sulfate Column I: The dialyzed PShepI-containing enzyme solution was applied to a CS column (2.5×30 cm) and equilibrated with 3 column volumes of a 25 mM Tris-HCl (containing 10 mM $CaCl_2$, pH 7.0) buffer. The column was then eluted with a gradient of the same buffer containing 0-1 M sodium chloride. The fractions with enzyme activity were detected and dialyzed against 2 L of 25 mM Tris-HCl (containing 10 mM $CaCl_2$, pH 7.0) buffer overnight.

Purification of PShepI by Cellufine Sulfate Column II: The dialyzed enzyme solution after the previous step was taken out and loaded onto a well-equilibrated CS column of the same size. The column was equilibrated with 3 column volumes of a 25 mM Tris-HCl (containing 10 mM $CaCl_2$, pH 7.0) buffer containing 0.15 M sodium chloride, and then eluted with a gradient of the same buffer containing 0.15-0.6 M sodium chloride. The fractions with enzyme activity were detected and dialyzed overnight.

Purification of PShepI by SP Column: The dialyzed enzyme solution after the previous step was loaded to a well-equilibrated SP column (specification: 2.5×30 cm). The column was then equilibrated with 3 column volumes of a 25 mM Tris-HCl (containing 10 mM $CaCl_2$, pH 7.0) buffer, and then eluted with a gradient of the same buffer containing 0-0.5M sodium chloride. The heparinase activity was detected. Detection of an undesired enzyme which can remove the sulphate from carbohydrate chain was carried out for single fractions with enzyme activity, the fractions with no such reactions and with IIS content of less than 1% after heparin treatment were collected, which has basically no impurity band. Finally, the products were concentrated in a 30K ultrafiltration centrifuge tube. The concentrated enzyme is PShepI enzyme with high-purity. The concentrated enzyme is made up to 0.5 ml with the corresponding buffer and mixed with glycerol in a 1:1 ratio and stored in a refrigerator at −20° C.

Purification of PShepII by Gradient Elution with Cellufine Sulfate Column I: The dialyzed PShepII fractions were loaded onto a 2.5×30 cm CS column equilibrated with a 25 mM Tris-HCl (containing 10 mM $CaCl_2$, pH 7.0) buffer. The column was equilibrated with 3 column volumes of the buffer containing 0.05 M sodium chloride and then eluted with a linear gradient of the same buffer containing 0.05-0.5 M sodium chloride. The fractions with enzyme activity were collected and dialyzed using 2 L 25 mM Tris-HCl (containing 10 mM $CaCl_2$, pH 7.0) buffer overnight.

Purification of PShepII by Isocratic Elution with Cellufine Sulfate Column II: The dialyzed PShepII fractions after the previous step were loaded onto a 2.5×30 cm CS column equilibrated with a 25 mM Tris-HCl (containing 10 mM CaCl 2, pH 7.0) buffer. The column was then equilibrated with 3 column volumes of the same buffer. The fractions with enzyme activity were then collected by isocratic elution with the same buffer containing 0.25 M sodium chloride.

Concentration of PShepII by Cellufine Sulfate Column III: The active PShepII fractions after isocratic elution in the previous step were added to 1 volume of 25 mM Tris-HCl (containing 10 mM $CaCl_2$), pH 7.0) buffer and loaded onto an equilibrated 2.5×30 cm CS column. The column was equilibrated with 3 column volumes of the same buffer, and then eluted with a gradient of the same buffer containing 0-0.5 M sodium chloride. The fractions with enzyme activity were separately subjected to a detection of undesired enzyme which can remove the sulphate from carbohydrate chain. The fractions with no undesired enzyme reactions and with IIS content of less than 1% after heparin treatment were collected, which is the new enzyme PShepII with high-purity. SDS-PAGE was performed to confirm that it is the basically free of impurity band. The high-purity PShepII was concentrated using a 30 KD ultrafiltration centrifuge tube, and mixed with 1 volume of glycerol and stored in a refrigerator at −20° C.

The enzyme activity, protein content, (specific activity) purification ratio, and (total activity) yield of PShepI and PShepII after each step are shown in Table 2 and Table 3, respectively.

TABLE 2

Enzyme activity and protein content of each step of PShepI purification by Method I

| PShepI purification step | Total volume (ml) | Total protein (mg) | HEP enzyme activity (IU/ml) | Total activity (IU) | Specific activity (IU/mg) | Purification ratio | Yield (%) |
|---|---|---|---|---|---|---|---|
| Crude enzyme | 461.00 | 231.71 | 0.48 | 220.12 | 0.95 | / | / |
| Ammonium sulfate precipitation | 415.00 | 144.93 | 0.51 | 211.60 | 1.46 | 1.54 | 96.13 |
| Q Column | 75.00 | 10.53 | 0.76 | 56.00 | 5.32 | 5.60 | 25.44 |
| CS-I Column | 30.00 | 3.88 | 1.35 | 40.50 | 10.45 | 11.00 | 18.41 |
| CS-II Column | 45.00 | 2.18 | 0.65 | 29.00 | 13.31 | 30.53 | 13.17 |
| SP Column | 1.00 | 0.50 | 12.80 | 12.80 | 25.60 | 26.95 | 5.81 |

TABLE 3

Enzyme activity and protein content of each step of PShepII purification by Method I

| PShepII Purification step | Total volume (ml) | Total protein (mg) | HEP enzyme activity (IU/ml) | Total activity (IU) | Specific activity (IU/mg) | Purification ratio | Yield (%) |
|---|---|---|---|---|---|---|---|
| Crude enzyme | 461.00 | 231.71 | 0.48 | 220.12 | 0.95 | / | / |
| Ammonium sulfate precipitation | 415.00 | 144.93 | 0.51 | 211.6 | 1.46 | 1.54 | 96.13 |
| Q Column | 99.00 | 18.11 | 0.45 | 40.00 | 2.21 | 2.33 | 18.17 |
| CS-I Column | 31.00 | 3.88 | 0.52 | 16.00 | 4.12 | 4.34 | 7.27 |
| CS-II Column | 22.00 | 1.94 | 0.64 | 14.00 | 7.20 | 7.58 | 6.36 |
| Sephadex G-100 | 1.00 | 0.46 | 8.20 | 8.20 | 18.00 | 18.95 | 3.73 |

Preparation Method II

Q-Sepharose Fast Flow column separation: The dialyzed crude enzyme solution prepared by the above ammonium sulfate precipitation was loaded onto a standard 2.5×30 cm Q-Sepharose Fast Flow column equilibrated with a 25 mM Tris-HCl (containing 10 mM $CaCl_2$, pH 7.0) buffer, and the column was equilibrated with 3 column volumes of the same buffer. A linear gradient elution with 0-1 M sodium chloride in the same buffer was performed. Fractions with enzyme activity were detected, labeled as PShepII, collected and dialyzed with 2 L 25 mM Tris-HCl (containing 10 mM $CaCl_2$, pH 7.0) buffer overnight. The loading flow-through and the equilibrating flow-through were detected, and the fractions with enzyme activity were collected and labeled as PShepI.

Purification of PShepI by SP column: The PShepI-containing enzyme solution obtained in the previous step was loaded onto a 2.5×30 cm SP-Sepharose Fast Flow equilibrated with a 25 mM Tris-HCl (containing 10 mM $CaCl_2$, pH 7.0) buffer. The column was equilibrated with 3 column volumes of the same buffer and then eluted with a linear gradient of the same buffer containing 0-0.5 M sodium chloride. The active fractions were collected and dialyzed against 2 L of 25 mM Tris-HCl (containing 10 mM $CaCl_2$, pH 7.0) buffer overnight.

Purification of PShepI by Cellufine Sulfate column: The enzyme solution obtained in the previous step was loaded onto a 2.5×30 cm Cellufine Sulfate column equilibrated with a 25 mM Tris-HCl (containing 10 mM $CaCl_2$, pH 7.0) buffer, and the column was then equilibrated with 3 column volumes of the same buffer containing 0.15 M sodium chloride, and then eluted with a linear gradient of the same buffer containing 0.15-0.6 M sodium chloride. The active fractions were collected, pooled, and concentrated through ultrafiltration to 1 mL by a 30 kD ultrafiltration centrifuge tube.

Purification of PShepII by linear gradient elution with Cellufine Sulfate-I: The dialyzed enzyme solution separated by Q column was loaded onto a standard 2.5×30 cm Cellufine Sulfate column equilibrated with a 25 mM Tris-HCl (containing 10 mM $CaCl_2$, pH 7.0) buffer, and the column was then equilibrated with the same buffer containing 0.05 M sodium chloride, provided with gradient elution with a buffer containing 0.05-0.5 M sodium chloride. The active fractions were collected and dialyzed against a 25 mM Tris-HCl (containing 10 mM $CaCl_2$, pH 7.0) buffer overnight.

Purification of PShepII by isocratic elution with Cellulide Sulfate-II column: The dialyzed enzyme solution from the previous step was loaded again onto a standard 2.5×30 cm Cellufine Sulfate column equilibrated with a 25 mM Tris-HCl (containing 10 mM $CaCl_2$, pH 7.0) buffer, and then isocraticaly eluted with 800 ml of the same buffer containing 0.25 M sodium chloride. The active fractions were then collected.

Cellufine Sulfate-III column concentration: One volume of 25 mM Tris-HCl (containing 10 mM $CaCl_2$, pH 7.0) buffer was added to the active PShepII solution after isocratic elution, and loaded onto a 2.5×30 cm CS column equilibrated with a 25 mM Tris-HCl (containing 10 mM $CaCl_2$, pH 7.0) buffer. The column was equilibrated with the same buffer, and then eluted with a linear gradient of the same buffer containing 0-0.5 M sodium chloride. The active fractions were collected, pooled and concentrated to 1 mL by ultrafiltration using a 30 kD ultrafiltration centrifuge tube.

The enzyme activity and protein content obtained in each step of the purification process are shown in Tables 4 and 5 below:

TABLE 4

Enzyme activity and protein content of each step of PShepI purification in Method II

| PShepI purification step | Total volume (ml) | Total protein (mg) | HEP enzyme activity (IU/ml) | Total activity (IU) | Specific activity (IU/mg) | Purification ratio | Yield (%) |
|---|---|---|---|---|---|---|---|
| Crude enzyme | 461.00 | 231.71 | 0.48 | 220.12 | 0.95 | / | / |
| Precipitation of ammonium sulfate | 415.00 | 144.93 | 0.51 | 211.60 | 1.46 | 1.54 | 96.13 |
| Q Column | 115.08 | 41.66 | 1.18 | 135.80 | 3.26 | 3.43 | 61.69 |

TABLE 4-continued

Enzyme activity and protein content of each step of PShepI purification in Method II

| PShepI puri- fication step | Total volume (ml) | Total protein (mg) | HEP enzyme activity (IU/ml) | Total activity (IU) | Specific activity (IU/mg) | Puri- fi- cation ratio | Yield (%) |
|---|---|---|---|---|---|---|---|
| SP Column | 54.00 | 9.49 | 1.91 | 103.14 | 10.87 | 11.44 | 46.86 |
| CS Column | 1.00 | 1.35 | 57.70 | 57.70 | 42.70 | 44.95 | 26.21 |

TABLE 5

Enzyme activity and protein content of each step of PShepII purification in Method II

| PShepII Puri- fication step | Total volume (ml) | Total protein (mg) | HEP enzyme activity (IU/ml) | Total activity (IU) | Specific activity (IU/mg) | Puri- fi- cation ratio | Yield (%) |
|---|---|---|---|---|---|---|---|
| Crude enzyme | 461.00 | 231.71 | 0.48 | 220.12 | 0.95 | / | / |
| Precipi- tation of ammo- nium sulfate | 415.00 | 144.93 | 0.51 | 211.6 | 1.46 | 1.54 | 96.13 |
| Q Column | 99.00 | 18.11 | 0.45 | 40.00 | 2.21 | 2.33 | 18.17 |
| CS-I Column | 31.00 | 3.88 | 0.52 | 16.00 | 4.12 | 4.34 | 7.27 |
| CS-II Column | 1.00 | 1.94 | 0.64 | 14.00 | 7.20 | 7.58 | 6.36 |

Example 3: Characterization of Heparinase PShepI and PShepII

The molecular weight of PShepI was approximately 74700 Da as determined by SDS-PAGE. The exact molecular weight of PShepI was 74791 Da as determined by MALDI-TOF-MS mass spectrometry. The isoelectric point of PShepI was 7.77 as determined by isoelectric focusing electrophoresis.

The molecular weight of PShepII was about 94000 Da as determined by SDS-PAGE, and the exact molecular weight was 94716 Da as determined by MALDI-TOF-MS mass spectrometry. The isoelectric point of PShepII was 5.76 as determined by isoelectric focusing electrophoresis.

The heparan sulfate (HS) substrate was dissolved in a 25 mM Tris-HCl (containing 10 mM $CaCl_2$, pH 7.0) buffer to prepare a heparan sulfate solution at a concentration of 1 mg/mL. The concentration of heparan sulfate substrate was set to 0.1, 0.2, 0.4, 0.6, 0.8, 1.0 mg/mL, respectively, and the activity of the enzyme at various heparan sulfate substrate concentrations was measured to calculate the Michaelis constant of the enzyme for heparan sulfate.

The heparin (HEP) substrate was dissolved in a 25 mM Tris-HCl (containing 10 mM $CaCl_2$, pH 7.0) buffer to prepare a heparin solution at a concentration of 1 mg/mL. The concentration of heparin substrate was set to 0.01, 0.03, 0.05, 0.1, 0.2, 0.4, 0.5, 0.6, 0.8, 1.0 mg/mL, respectively, and the activity of the enzyme at various heparin substrate concentrations was measured to calculate the Michaelis constant of the enzyme for heparin. The initial rate of the enzyme reaction under each condition was determined at different substrate concentrations to determine the Michaelis constant.

It was determined that the Michaelis constants of PShepI were 4.20 and 0.28, respectively, when HEP and HS were used as substrates. It was determined that the Michaelis constants of PShepII were 0.09 and 0.25, respectively, when HEP and HS were used as substrates.

Example 4: Substrate Specificity and Product Specificity of PShepI and PShepII

Study on substrate specificity of PShepI: Activity of PShepI was determined using heparin (HEP), heparan sulfate (HS), chondroitin sulfate (CS), and dermatan sulfate (DS) as substrates respectively. It was found that PShepI had no enzymatic activity when CS and DS were used as substrates, but had enzymatic activity when HEP and HS were used as substrates, and the activity ratio was about HEP:HS=0.87:1.

Study on substrate specificity of PShepII: Activity of PShepII was determined using heparin (HEP), heparan sulfate (HS), chondroitin sulfate (CS), and dermatan sulfate (DS) as substrates respectively. It was found that the PShepII enzyme had no enzymatic activity when CS and DS were used as substrates, but had enzymatic activity when HEP and HS were used as substrates, and the activity ratio was about HEP:HS=1:4.3.

Figure 1:
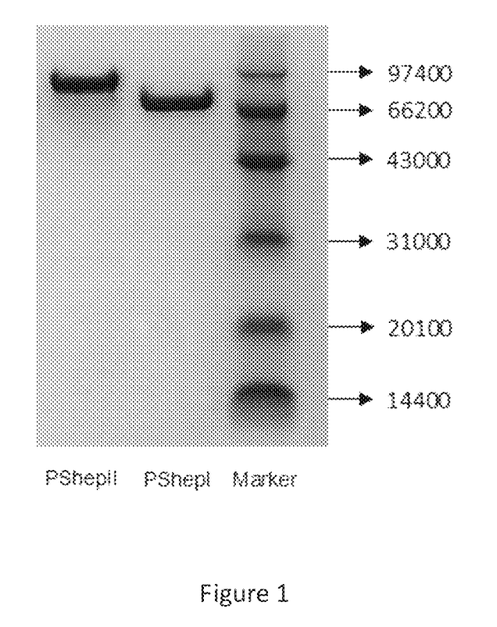
FIG. 1 shows a SDS-PAGE image of the purified PShepI, PShepII.
Figure 2:
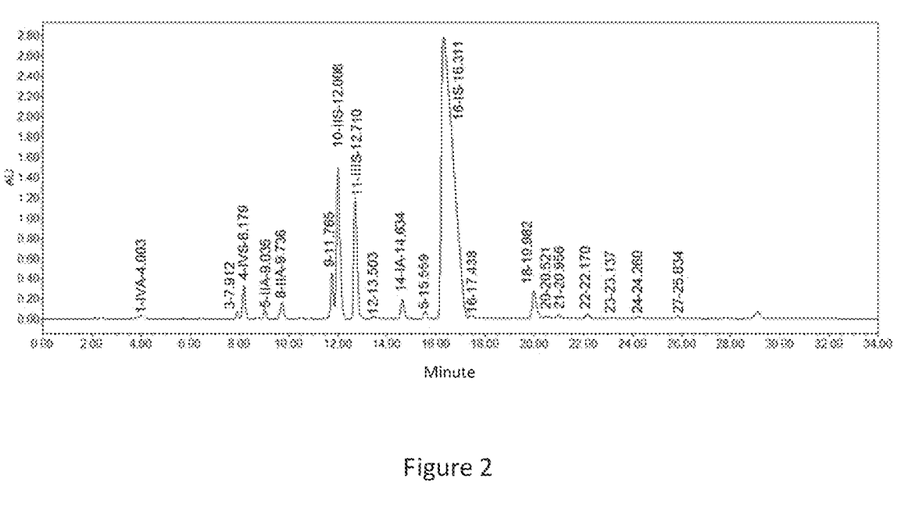
FIG. 2 is a liquid chromatographic image of the enzymolysis product of HEP by PShepI.

Disaccharide analysis on PShepI enzymatic hydrolysis of HEP: 3 IU (heparin-based enzyme activity) of PShepI was added to 50 mg heparin, and made up with 25 mM Tris-HCl (containing 10 mM $CaCl_2$), pH 7.0) buffer to 500 μl, 37° C. for 24 h for enzymatic hydrolysis, then placed in a 100° C. water bath for inactivattion for 5 minutes, and then liquid phase analysis was carried out for the disaccharide component of the sample. The results are shown in FIG. 2. After enzymatic hydrolysis of HEP by PShepI, the main disaccharide components of the product were IIS and IS, where the peak area of IS accounted for 67.92%.

Example 5: Sequencing of Heparinase PShepI

The genomic DNA of the Z7 *Pseudomonas stutzeri* strain was extracted by using the "TIANamp Bacteria DNA Kit Bacterial Genomic DNA Extraction Kit" according to the instructions of the kit. Thereafter, the extracted genomic DNA of the Z7 *Pseudomonas stutzeri* strain was sequenced to obtain the genome sequence of the Z7 *Pseudomonas stutzeri* strain.

The PShep I enzyme isolated and purified from the Z7 *Pseudomonas stutzeri* was subjected to in-gel digestion by Kumarathan method (K method for short), followed by MALDI analysis to obtain a peptide spectrum of the heparinase PShepI. The protein sequence information obtained by the peptide spectrum is aligned with the ORF obtained from the genomic sequence of the Z7 strain, to finally obtain the coding sequence (1971 bp, SEQ ID NO:1) and the amino acid sequence (656 amino acid residues, SEQ ID NO:2) of PShepI.

Example 6: Preparation of PShepI Engineered Bacterium

In order to further increase the yield of PShep I (the enzyme yield of the Z7 strain was about 150 IU/L), the inventors performed codon optimization to the coding sequence of PShepI according to the codon preference of *E.* coli BL21 (DE3), and added a 6×His tag (SEQ ID NO: 3) to the N-terminus of the PShep I enzyme. The corresponding coding sequence was cloned into the pET-30a vector and then transformed into the *E. coli* BL21 (DE3) strain to obtain an engineered strain. The engineered bacterium was fermented to obtain an engineered enzyme with a yield of up to about 10000 IU/L (the yield of the Z7 strain was about 150 IU/L). The 232 nm endpoint absorbance value, molecular weight, potency and yield in hydrolyzing heparin of the engineered enzyme and the wildtype enzyme were consistent, and thus it was confirmed that the engineered enzyme and the wildtype enzyme had substantially the same properties.

The invention claimed is:

1. A recombinant heparinase comprising an amino acid sequence shown in SEQ ID NO:2,
wherein the recombinant heparinase comprises a linker or is fused to a tag, wherein the linker and/or tag facilitates the production of the recombinant heparinase in a host cell of interest, increases the amount of expression or increases the soluble expression, facilitates the isolation and purification of the recombinant heparinase, but do not substantially affect the activity of the recombinant heparinase.

2. An expression construct, comprising a nucleotide sequence encoding the heparinase comprising an amino acid sequence shown in SEQ ID NO:2, operably linked to an expression control sequence.

3. A recombinant host cell, which is transformed with the expression construct of claim 2.

4. A method for producing a heparinase, comprising:
a) culturing the host cell of claim 3 under a condition that allows the expression of the heparinase;
b) obtaining the heparinase expressed by the host cell from the culture obtained from step a); and
c) optionally further purifying the heparinase obtained from step b).

5. A method for producing heparinase which comprises: culturing a *Pseudomonas stutzeri* strain deposited at the China Center for Type Culture Collection under the Accession Number CCTCC M 2017174; lysing the cultured cells of the *Pseudomonas stutzeri* strain; and isolating and/or purifying the heparinase from the lysate.

6. A method for producing heparinase, wherein the method comprises the steps of:
a) culturing a *Pseudomonas stutzeri* strain deposited at the China Center for Type Culture Collection under the Accession Number CCTCC M 2017174 and collecting the cultured bacterial cells;
b) resuspending and lysing the cells obtained in step a) in a buffer, and collecting the supernatant after centrifugation;
c) precipitating the supernatant obtained in step b) with ammonium sulfate of 20% to 100% saturation, and dissolving the resulting precipitate in a buffer and dialyzing against the buffer;
d) loading the product of step c) onto an anion exchange column, equilibrating the column with a buffer, and collecting the loading flow-through and the equilibrating flow-through, and dialyzing the collected loading flow-through and the equilibrating flow-through against the buffer;
e) loading the product of step d) onto a cation exchange column, and equilibrating the column with a buffer, performing linear gradient elution with a sodium chloride solution based on the same buffer, collecting fractions of the eluate with heparinase activity, and optionally dialyzing the collected eluate against the buffer.

7. The method of claim 6, wherein
the method further comprises the steps of:
f) loading the product of step e) onto a heparinase affinity column, and equilibrating the column with a buffer, performing linear gradient elution with a sodium chloride solution based on the same buffer, collecting fractions of the eluate with heparinase activity, and optionally dialyzing the collected eluate against the buffer.

8. The method of claim 7, wherein the heparinase affinity column is selected from a Cellufine Sulfate column and a heparin-conjugated CNBr-activated Sepharose CL-4B heparinase affinity column; and the sodium chloride solution is a 0.15-0.6M sodium chloride solution.

9. The method of claim 6, wherein the anion exchange column is selected from Q-Sepharose Fast Flow, Q-Sepharose Big Beads, Q-Sepharose XL and Q-Sepharose High Performance columns; the cation exchange column is a SP-Sepharose Fast Flow column; and the sodium chloride solution is a 0-0.5M sodium chloride solution.

10. The method of claim 6, wherein the heparinase has one or more characteristics selected from the group consisting of:
i) a molecular weight of 74791 Da;
ii) an isoelectric point of 7.77;
iii) a HEP/HS enzyme activity ratio of 0.87:1 with heparin (HEP) and HS (heparan sulfate) as the substrates;
iv) a Michaelis constant of 4.20 with HEP as the substrate;
v) a Michaelis constant of 0.28 with HS as the substrate; and
vi) when HEP is used as the substrate, the major heparin disaccharide products are IIS and IS.

11. A method for producing heparinase, wherein the method comprises the steps of:
a) culturing a *Pseudomonas stutzeri* strain deposited at the China Center for Type Culture Collection under the Accession Number CCTCC M 2017174 and collecting the cultured bacterial cells;
b) resuspending and lysing the cells obtained in step a) in a buffer and collecting the supernatant after centrifugation;
c) precipitating the supernatant obtained in step b) with ammonium sulfate of 20% to 100% saturation, and dissolving the resulting precipitate in a buffer and dialyzing against the buffer;
d) loading the product of step c) onto an anion exchange column, and equilibrating the column with a buffer, performing linear gradient elution with a sodium chloride solution based on the same buffer, collecting fractions of the eluate with heparinase activity, and optionally dialyzing the collected eluate against the buffer.

12. The method of claim 11, wherein the method further comprises the steps of:
e) loading the product of step d) onto a heparinase affinity column, and equilibrating the column with a buffer, performing linear gradient elution with a sodium chloride solution based on the same buffer, collecting fractions of the eluate with heparinase activity, and dialyzing the collected eluate against the buffer;
f) loading the product of step e) onto a heparinase affinity column, and equilibrating the column with a buffer, performing isocratic elution with a sodium chloride solution based on the same buffer, and collecting fractions of the eluate with heparinase activity; and
g) loading the product of step f) onto a heparinase affinity column, and equilibrating the column with a buffer, performing linear gradient elution with a sodium chloride solution based on the same buffer, collecting fractions of the eluate with heparinase activity, and optionally dialyzing the collected eluate against the buffer.

13. The method of claim 12, wherein the heparinase affinity column is a Cellufine Sulfate column; the sodium chloride solution in step e) is a 0.05-0.5M sodium chloride solution; the sodium chloride solution in step f) is a 2.5M sodium chloride solution; and the sodium chloride solution in step g) is a 0-0.5M sodium chloride solution.

14. The method of claim 11, wherein the anion exchange column is selected from Q-Sepharose Fast Flow, Q-Sepharose Big Beads, Q-Sepharose XL and Q-Sepharose High Performance columns; and the sodium chloride solution is a 0-0.5M sodium chloride solution.

15. The method of claim 11, wherein the heparinase has one or more characteristics selected from the group consisting of:
   i) a molecular weight of 94716 Da;
   ii) an isoelectric point of 5.76;
   iii) a HEP/HS enzyme activity ratio of 1:4.3 with heparin (HEP) and HS (heparan sulfate) as the substrates;
   iv) a Michaelis constant of 0.09 with HEP as the substrate; and
   v) a Michaelis constant of 0.25 with HS as the substrate.

16. A method for producing a low molecular weight heparin or an ultra-low molecular weight heparin, comprising the step of contacting the heparin with the heparinase obtained by the method of claim 5, 6 or 11.

17. A method for producing a low molecular weight heparin or an ultra-low molecular weight heparin, comprising the step of contacting the heparin with the recombinant heparinase comprising an amino acid sequence shown in SEQ ID NO:2.

18. A method for producing a low molecular weight heparin or an ultra-low molecular weight heparin, comprising the step of contacting the heparin with the host cell of claim 3.

* * * * *